United States Patent
Su

(10) Patent No.: US 10,448,820 B2
(45) Date of Patent: Oct. 22, 2019

(54) EYE IMAGING APPARATUS WITH SEQUENTIAL ILLUMINATION AND A SYNTACTIC IMAGE ANALYZING METHOD

(71) Applicant: VISUNEX MEDICAL SYSTEMS CO. LTD., Grand Cayman (KY)

(72) Inventor: Wei Su, Sunnyvale, CA (US)

(73) Assignee: VISUNEX MEDICAL SYSTEMS CO. LTD., Grand Cayman (KY)

( * ) Notice: Subject to any disclaimer, the term of this patent is extended or adjusted under 35 U.S.C. 154(b) by 0 days.

(21) Appl. No.: 15/563,405

(22) PCT Filed: Mar. 31, 2016

(86) PCT No.: PCT/US2016/025260
§ 371 (c)(1),
(2) Date: Sep. 29, 2017

(87) PCT Pub. No.: WO2016/161110
PCT Pub. Date: Oct. 6, 2016

(65) Prior Publication Data
US 2018/0084989 A1 Mar. 29, 2018

Related U.S. Application Data

(60) Provisional application No. 62/141,231, filed on Mar. 31, 2015.

(51) Int. Cl.
*H04N 5/225* (2006.01)
*G06T 3/00* (2006.01)
(Continued)

(52) U.S. Cl.
CPC .......... *A61B 3/0025* (2013.01); *A61B 3/0008* (2013.01); *A61B 3/0041* (2013.01);
(Continued)

(58) Field of Classification Search
CPC ............... H04N 5/2256; G06T 5/50; G06T 2207/10152; A61B 3/0025; A61B 3/14
See application file for complete search history.

(56) References Cited

U.S. PATENT DOCUMENTS

| 2007/0244393 A1* | 10/2007 | Oshiki ............... A61B 5/02007 600/463 |
| 2013/0271728 A1 | 10/2013 | Ranchod et al. |
| 2015/0009473 A1* | 1/2015 | Su ........................ A61B 3/125 351/206 |

OTHER PUBLICATIONS

Extended European Search Report received in corresponding European Application No. 16774194 dated Nov. 26, 2018.

* cited by examiner

Primary Examiner — Tsion B Owens
(74) Attorney, Agent, or Firm — Arent Fox LLP

(57) ABSTRACT

Various embodiments of the disclosure comprise an eye imaging system including an eye imaging apparatus and an eye imaging computing apparatus. The eye imaging apparatus can be configured to receive a plurality of images of the eye with a same field of view while each portion of the eye is illuminated time-sequentially. The image computing apparatus can comprise an image processing unit configured to combine the plurality of images into a composite image. Various embodiments of the disclosure comprise a syntactic image analyzing method. The syntactic image analyzing method can comprise aligning a plurality of images of an eye with a same field of view and combining the plurality of images into a composite image. The image analyzing method can further comprise analyzing each image by identifying a boundary line of a clear portion and gradually removing an unclear portion in each image.

19 Claims, 6 Drawing Sheets

(51) Int. Cl.
*A61B 3/00* (2006.01)
*A61B 3/14* (2006.01)
*A61B 3/12* (2006.01)
*G06T 7/13* (2017.01)
*A61B 5/00* (2006.01)
*G06T 5/50* (2006.01)
*G06T 7/00* (2017.01)
*H04N 5/232* (2006.01)
*G06T 5/00* (2006.01)
*G06K 9/00* (2006.01)

(52) U.S. Cl.
CPC .................. *A61B 3/12* (2013.01); *A61B 3/14* (2013.01); *A61B 5/0013* (2013.01); *G06T 3/0068* (2013.01); *G06T 5/008* (2013.01); *G06T 5/50* (2013.01); *G06T 7/0012* (2013.01); *G06T 7/0014* (2013.01); *G06T 7/13* (2017.01); *H04N 5/2256* (2013.01); *H04N 5/23293* (2013.01); *G06K 2009/00932* (2013.01); *G06K 2209/05* (2013.01); *G06T 2207/10152* (2013.01); *G06T 2207/20221* (2013.01); *G06T 2207/30041* (2013.01); *G06T 2207/30101* (2013.01)

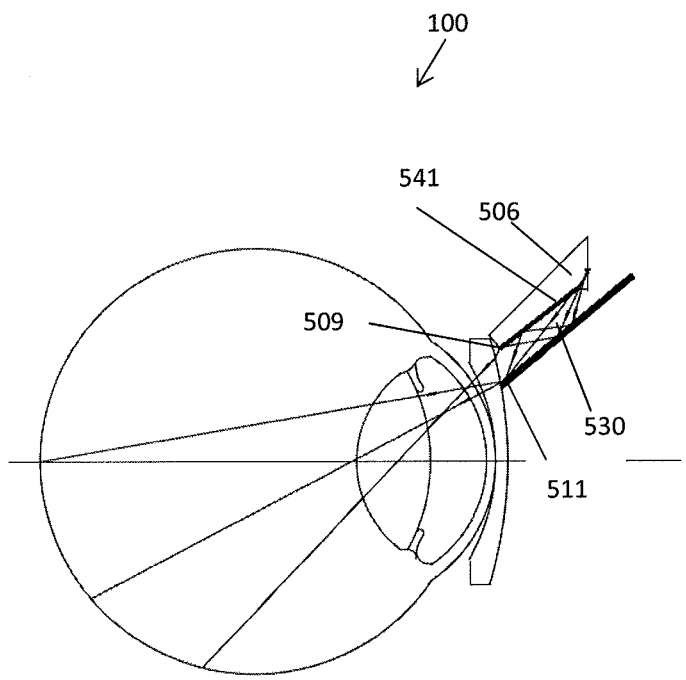
FIG. 3
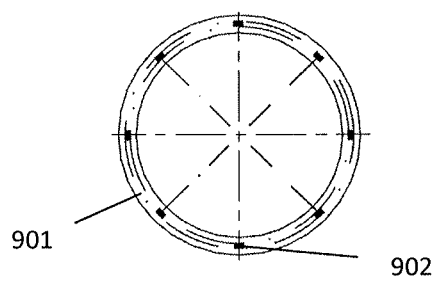     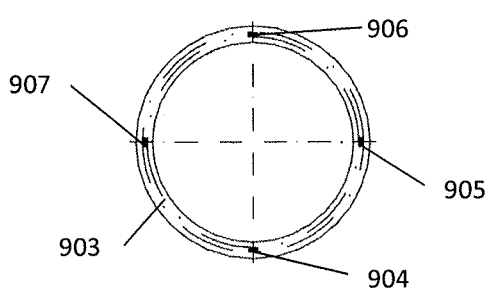
FIG. 4                  FIG. 5

700

930

EYE IMAGING APPARATUS WITH SEQUENTIAL ILLUMINATION AND A SYNTACTIC IMAGE ANALYZING METHOD

CROSS REFERENCE TO RELATED APPLICATIONS

This application claims the benefit of U.S. Application No. 62/141,231, titled: "AN EYE IMAGING APPARATUS WITH SEQUENTIAL ILLUMINATION AND A SYNTACTIC IMAGE ANALYZING METHOD", filed Mar. 31, 2015, which is incorporated herein by reference.

INCORPORATION BY REFERENCE

The following U.S. patent applications are herein incorporated by reference in their entirety: U.S. application Ser. No. 14/191,291, titled "EYE IMAGING APPARATUS WITH A WIDE FIELD OF VIEW AND RELATED METHODS", and filed on Feb. 26, 2014, which is a continuation-in-part of U.S. application Ser. No. 13/845,069, titled "IMAGING AND LIGHTING OPTICS OF A CONTACT EYE CAMERA", and filed on Mar. 17, 2013, and U.S. patent application Ser. No. 14/312,590, titled "MECHANICAL FEATURES OF AN EYE IMAGING APPARATUS", filed on Jun. 23, 2014.

All publications and patent applications mentioned in this specification are herein incorporated by reference in their entirety to the same extent as if each individual publication or patent application was specifically and individually indicated to be incorporated by reference.

FIELD

Various embodiments of the disclosure relate generally to an eye imaging apparatus, an eye imaging system and related methods, and for example to an eye imaging apparatus with sequential illumination and an eye imaging system with a syntactic image analyzing method.

BACKGROUND

Eyes are among the most valued human organs that play indispensable roles in life. Likewise, eye diseases and vision loss in general are serious problems. Moreover, eye diseases and vision problems among children, especially new-born babies, can have severe and far-reaching implications. For infants and small children, the visual centers in the brain are not fully mature. For the visual centers in the brain to develop properly, proper input from both eyes is desirable. Therefore good vision can be an important factor in the proper physical development and educational progress. Undetected eye problems in infants and others may result in irreversible loss of vision. Early detection and diagnosis provide the best opportunity for treatment and prevention of vision loss.

In eye examinations, eye imaging apparatus has become increasingly important. Since retinal and optic nerve problems are among the leading causes in vision loss, eye imaging apparatus capable of imaging a posterior segment of the eye can be particularly useful. Moreover, an eye imaging apparatus with a wide field of view can offer the benefit of enabling evaluation of pathologies located on the periphery of the retina. However, because of the complicated structure of the eye, the reflection and scattering from the eye can cause glare and haze, which obscures the images acquired by an eye imaging apparatus. Thus the images from the posterior segment of the eye with a wide field of view often exhibit a layer of strong haze or glare. This problem is especially acute for the patients with dark pigmentation in the eyes. There is a need for an eye imaging system that is capable to obtain high quality images of the eye and a novel image processing method to achieve the high quality images.

SUMMARY OF THE DISCLOSURE

The present disclosure relates to an eye imaging apparatus, an eye imaging system and an eye image processing method.

Various embodiments disclosed herein comprise an eye imaging apparatus. The eye imaging apparatus can comprise a housing, a light source disposed inside the housing comprising a plurality of light emitting elements each configured to illuminate a different portion of an eye time-sequentially. The eye imaging apparatus can comprise an optical imaging system disposed inside the housing which comprises an optical window having a concave front surface configured to receive a portion of the eye. The eye imaging apparatus can comprise an image sensor disposed inside the housing configured to receive a plurality of images of the eye with a same field of view through the optical imaging system while each portion of the eye is illuminated time-sequentially by one of the light emitting elements. The eye imaging apparatus can comprise a computing and communication unit disposed inside the housing. The computing and communication unit can comprise an image processing unit configured to analyze the plurality of images to identify a clear portion in each of the plurality of images and process the plurality of images into a single composite image. The computing and communication unit can further comprise a display configured to display the plurality of images and the single composite image; and a wireless communication device configured to receive and transmit the plurality of images and the single composite image.

Various embodiments of the disclosure comprise syntactic image analyzing method to process a plurality of images of an eye with a same field of view under sequential illumination into a composite image. The syntactic image analyzing method can comprise identifying a plurality of reference points in each of the plurality of images. The syntactic image analyzing method can comprise analyzing each of the plurality of images to identify a boundary line of a clear portion in each of the plurality of images and adjusting the boundary line by gradually decreasing brightness of pixels near the boundary line away from the clear portion in each of the plurality of images. The syntactic image analyzing method can further comprise aligning the plurality of images by using the plurality of reference points, and combining the plurality of images into a single composite image.

Various embodiments of the disclosure comprise an eye imaging system. The eye imaging system can comprise an eye imaging apparatus and an eye imaging computing apparatus. The eye imaging apparatus can comprise a housing, a light source disposed inside the housing. The light source can comprise a plurality of light emitting elements configured to illuminate different portions of an eye time-sequentially. The eye imaging apparatus can further comprise an optical imaging system disposed inside the housing. The optical imaging system can comprise an optical window configured to receive a portion of the eye. In some embodiments, the curvature of the outer surface of the optical window can substantially match the curvature of a cornea of an eye. The eye imaging apparatus can further comprise an image sensor disposed inside the housing configured to receive a plurality of images of the eye with a same field of view through the optical imaging system while each portion of the eye is illuminated time-sequentially. The eye imaging apparatus can further comprise a computing and communication unit disposed inside the housing configured to receive and transmit the plurality of images. The plurality of images can be transferred to the image computing apparatus. The image computing apparatus can comprise an image processing unit. The image processing unit can be configured to combine the plurality of images into a composite image. The image computing apparatus can be configured to receive the plurality of images from and transmit the composite image to the eye imaging apparatus. In some embodiments, the computing and communication unit of the eye imaging apparatus can comprise a touch screen display configured to display the composite image received from the image computing apparatus.

In some embodiments, the image computing apparatus can be configured to identify a plurality of reference points in each image of the plurality of images. The plurality of reference points can comprise at least one of the blood vessels, the intersections of blood vessels, the nerves, the intersections of the nerves of a posterior segment of the eye. In some embodiments, the image processing unit can be configured to align the plurality of images by using a reference image. The reference image can be obtained with the same field of view as that of the plurality of images through the optical imaging system.

In some embodiments, the image computing apparatus can be configured to analyze each image of the plurality of images by identifying a boundary line of a clear portion and gradually removing an unclear portion. In some embodiments, the image processing unit can be configured to identify the boundary line based on a mean value of brightness of pixels at the boundary line. In some embodiments, the image processing unit can be configured to perform color calibration to the composite image.

Various embodiments of the disclosure comprise a syntactic image analyzing method. The syntactic image analyzing method can be used to combine a plurality of images of an eye with a same field of view under sequential illumination into a composite image. The syntactic image analyzing method can comprise identifying a plurality of reference points in each image of the plurality of images. The image analyzing method can further comprise analyzing each image by identifying a boundary line of a clear portion and gradually removing an unclear portion in each image.

In various embodiments, the syntactic image analyzing method can comprise aligning the plurality of images by using the plurality of reference points, and combining the plurality of images into a composite image. In some embodiments, the syntactic image analyzing method can comprise identifying the boundary line based on a mean value of brightness of pixels at the boundary line. The syntactic image analyzing method can further comprise determining a mean value of brightness of pixels at the boundary line by calculating a first average brightness of pixels at a first sample area and a second average brightness of pixels at a second sample area. In some embodiments, the syntactic image analyzing method can further comprise performing color calibration to the composite image.

In some embodiments, the syntactic image analyzing method can comprise aligning the plurality of images by using a reference image. The reference image can be received with the same field of view through the optical imaging system. In some other embodiments, the syntactic image analyzing method can comprise aligning each of the plurality of images to another adjacent image of the plurality of images.

Various embodiments disclose a non-transitory, computer-readable storage medium storing a set of instructions capable of being executed by a processor. When executed by the processor, the set of instructions can cause the processor to combine a plurality of images of an eye with a same field of view under sequential illumination into a composite image. The set of instructions can cause the processor to identify a plurality of reference points in each image of the plurality of images, analyze each image by identifying a boundary line of a clear portion and gradually and removing an unclear portion in each image. The set of instructions can further cause the processor to align the plurality of images by using the plurality of reference points and combine the plurality of images into a composite image. In some embodiments, the set of instructions, when executed by the processor, further causes the processor to identify the boundary line based on a mean value of brightness of pixels at the boundary line. The set of instructions can cause the process to determine a mean value of brightness of pixels at the boundary line by calculating a first average brightness of pixels at a first sample area and a second average brightness of pixels at a second sample area.

Various embodiments in this disclosure comprise a method of imaging an eye under sequential illumination. The method can comprise allowing a user to vary an intensity of a plurality of light emitting elements over time to illuminate different portions of an eye and allowing the user to image the eye through an optical imaging system. The optical imaging system can comprise an optical window configured to be in contact with a cornea of the eye. The method can allow a plurality of images of the eye with a same field of view through the optical imaging system to be received by an image sensor while each portion of the eye is illuminated time-sequentially. The method can further allow the plurality of images to be transmitted to an image computing apparatus. The method can comprise allowing the image computing apparatus to identify a plurality of reference points in each image of the plurality of images, analyze each image by identifying a boundary line of a clear portion and gradually removing an unclear portion, align the plurality of images and combine the plurality of images into a composite image.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 3 is a side view of a light conditioning element of the eye imaging apparatus according to some embodiments of the disclosure.

FIG. 4 schematically illustrates the distribution of the light emitting elements, where a total of 8 light emitting elements are used.

FIG. 5 schematically illustrates the distribution of the light emitting elements, where a total of 4 light emitting elements are used.

DETAILED DESCRIPTION

Various aspects of the present disclosure now will be described in detail with reference to the accompanying figures. These aspects of the disclosure may be embodied in many different forms and should not be construed as limited to the exemplary embodiments discussed herein.

Various embodiments of the present disclosure describe an eye imaging apparatus. In some embodiments, this eye imaging apparatus has a wide field of view. The field of view, may in certain embodiments be at least 60 degrees and up to 180 degrees. In some embodiments, the field of view is at least 120 degrees but no more than 180 degrees. Various embodiments of the eye imaging apparatus may, for example, comprise a housing, a light source inside the housing to illuminate an eye, and an optical imaging system inside the housing. The optical imaging system may include an optical window configured to be in contact with a cornea of the eye, an imaging lens positioned behind the optical window and optically aligned with the optical window, a light conditioning element having a multi-segment (e.g., reflective and/or refractive) surface configured to receive light from the light source and direct light to the eye, and an image sensor configured to receive light from the eye through the optical imaging system. In some embodiments, the light conditioning element is positioned behind a peripheral portion of the optical window. Also, in some embodiments, the imaging apparatus may further comprise a memory configured to temporarily store images, and a computing and communication subsystem including a touch screen monitor configured to receive, display and transmit the image.

Figure 1:
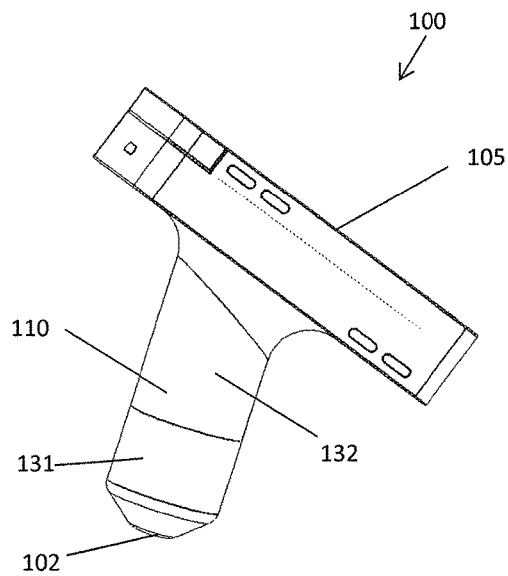
FIG. 1 is a perspective view that schematically illustrates a side view of an eye imaging apparatus according to various embodiments of the disclosure.

FIG. 1 schematically illustrates a side view of an eye imaging apparatus 100 according to various embodiments of the disclosure. The eye imaging apparatus 100 may be compact and in various embodiments has a size less than 250 mm along the longest dimension thereof. For example, in some embodiments the eye imaging apparatus may be between 250 mm and 200 mm, 150 mm, or 100 mm along the longest dimension. In some embodiments, the eye imaging apparatus may weigh less than 1 kg. For example, the eye imaging apparatus may weigh between 1 kg and 0.5 kg, or 0.3 kg, or 0.2 kg in some embodiments. The eye imaging apparatus may be carried by the users in a small carrying case with a handle, for example, that is less than 600 mm×400 mm×300 mm and weigh less than 15 kg or in another convenient manner due to its compactness. In some embodiments, for example, the carrying case is between (600 mm and 300 mm)×(400 mm and 200 mm)×(300 and 150 mm). Also, the carrying case weighs between 15 kg and 10 kg or 5 kg, in some embodiments. Sizes outside these ranges for the eye imaging system and the carrying case are also possible. Various embodiments may be easily operated by the operators with little training.

The imaging apparatus may have a portion constructed to be in a cylindrical shape to allow easy grabbing by one hand and usable as a handle with a display and/or user input interface such as a touch screen monitor 105 mounted at the top of cylindrical part 110. The users may precisely adjust the position/angle of the apparatus with one hand freeing another hand to work on other tasks, for example, opening the eyelids of the patient with the fingers.

Captured images may be transferred to other computing devices or internet based devices, like storage units, through wired or wireless communication systems. In some embodiments, the imaging apparatus is powered by a battery. Also in various embodiments, live images may be displayed on the touch screen monitor 105 or a larger display monitor that receives data from this imaging apparatus 100 in real time. The eye imaging apparatus 100 may be used as a diseases screening or medical diagnosis device for the ophthalmic applications. The eye imaging apparatus 100 may be used in remote rural areas where traveling to the eye care facilities is not convenient. The eye imaging apparatus 100 may also be used as a portable medical imaging device for other medical needs such as ENT or dermatology. Furthermore, the imaging apparatus 100 may have applications in areas other than medical applications, for example, for security screening applications where the images from the posterior/anterior segment of the eye may be used for personal identification purposes.

The eye imaging apparatus 100 may also be used to image the eyes of animals. For example, the eye imaging apparatus may be used, with or without modification of optics from its human use, to image or photograph the eyes of animals such as livestock, pets, and laboratory test animals, including horses, cats, dogs, rabbits, rats, guinea pigs, mice, etc.

The eye imaging apparatus 100 may comprise a front imaging module and a main module. The eye imaging apparatus 100 may be built as one piece or two separate pieces, as shown as 131 and 132, in FIG. 1. In some embodiments, the front imaging module 131 may be removed or replaced with other functioning modules which may contain different optics. For example, front imaging modules with higher magnification, front imaging modules designed for premature babies, front imaging modules designed for adults, front imaging modules designed for fluorescein angiography imaging, front imaging modules for NIR imaging and front imaging modules for anterior segment imaging can be used in different circumstances. Accordingly, in designs where the front imaging module is replaceable or removable, the eye imaging apparatus's potential use or applications may be significantly expanded.

An optical window 102 is exposed on the outside of the housing of the imaging apparatus enabling light to enter into and exit out of the housing. In various embodiments, the eye can be place proximal to or up against the optical window 102 to obtained images of the eye. The window 102 has central and peripheral portions. The central portion of the window is employed as the entrance into the housing for light reflected from the eye that is used to image the eye. The peripheral region of the window, which is disposed about the center, is configured for egress of light from the housing such as for example projecting light onto and/or into the eye to illuminate the eye.

In some embodiments, the imaging apparatus 100 may be used to acquire images of the posterior segment of the eye with various magnifications and under the illumination from broadband or narrow spectral light sources. The spectrum of the light source may be in the visible, IR, near IR, UV light range or combinations thereof. To obtain a wide field of the view (FOV), the optical window 102 may be placed over the cornea of the eye with slight pressure. Accordingly, the optical window 102 may have a concave surface matching the size of the cornea. In some embodiments, for example, the outer surface of the optical window 102 has a radius of curvature of between 6 mm and 15 mm. An optical transparent index matching gel with sufficient viscosity may be placed between the cornea and the optical window 102. The viscosity of the index matching gel may be at least 100 centipoise, 200 centipoise or 300 centipoise. The iris of the patient may or may not be dilated with special drugs. In some embodiments, the imaging apparatus 100 may also be used to obtain images of the anterior segment of the eye by using a front imaging module designed for imaging the anterior segment, using the same illumination system.

Figure 2:
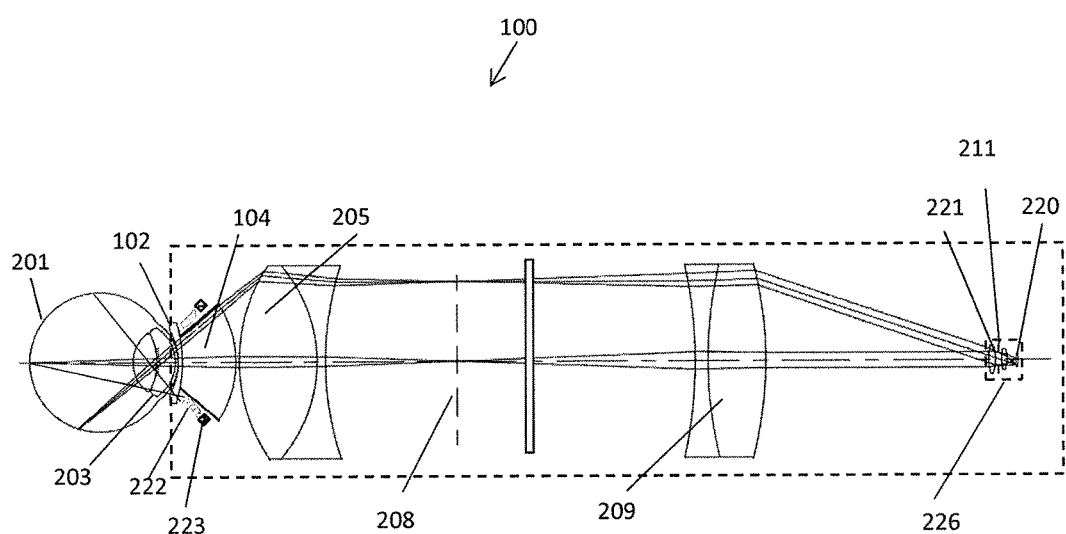
FIG. 2 is an example of the optical schematic that illustrates an optical design of an eye imaging apparatus according to various embodiments of the disclosure.

FIG. 2 schematically illustrates one embodiment of the optical design or optical system of the eye imaging apparatus 100, where the posterior segment of the eye 201 is imaged or photographed by the eye imaging apparatus 100. The eye imaging apparatus can comprise a light source 223 and a light conditioning element 222. The optical imaging system of the eye imaging apparatus includes an optical window 102 and an imaging lens 104. The optical window 102 is configured to be in contact with the cornea 203 and may have a concave surface that matched the curvature of the eye. In various embodiments, for example, the radius curvature of the outer surface of the optical window 102 is between about 6 mm and 15 mm. The imaging lens 104, which may include one or multiple lens elements, is positioned behind the optical window 102, on the opposite side of the window as the eye, and optically aligned with the optical window 102. The optical axis of the window 102 and imaging lens 104 may, for example, be substantially aligned with the optical axis of the eye in some cases but not all. For example, the practitioner may examine the eye in a manner that the optical axis of the imaging system is substantially aligned with the optical axis of the eye, however, in some cases, the practitioner tilts the eye imaging apparatus such that these axes are not aligned. Although the radius of the curvature for the frontal optical surface of the optical window 102 is chosen to closely match that of the cornea 203, the back surface of the optical window may be flattened out slightly depending on the design of the optical illumination system. The optical window 102 may be made from the same or different optical materials as the imaging lens 104. For a wide field of view optical imaging system, the use of the optical index matching gel between the optical window 102 and cornea 203 helps to eliminate significant amount of optical aberrations originated from the cornea of the eye. The curvature of the frontal surface of the imaging lens 104 may be the same as that of the back surface of the optical window 102, or different. The back surface of the imaging lens 104 may be either spherical or non-spherical to obtain desired result for the images. In some embodiments, a small gap of air or other material is placed between the optical window 102 and the imaging lens 104, although the two optical components may be in contact in certain areas or even bonded or affixed together with adhesive.

In some embodiments, the optical imaging system may further includes a first set of relay lenses 205 configured to form a secondary image 208 of the eye near a back focal plane of the first set of relay lenses 205, a second set of relay lenses 209 configured to project the secondary image 208 to infinity with a front focal plane positioned near the back focal plane of the first set of relay lenses 205. In various embodiments, a set of miniature lenses 221 is positioned near the back focal plane of the second set of relay lenses 209 and configured to deliver light from the eye to the image sensor 220. A miniature camera 226 comprising the miniature lens or lenses 221 and the sensor 220 has a format no more than 1/2.2 inches or 1/3.2 inches with a focal length of about 4 mm or less, for example between about 4 mm and 2 mm or 4 mm and 3 mm, etc. The view angle for the miniature lens or lenses 221 may be 75° or less with a sensor 220 appropriately sized based, for example, on the focal length of the miniature lens 221. The camera module 226, which includes the sensor chip 220 and the miniature lens or lenses 221 is about 8.5×8.5 mm, or between 10 mm×10 mm and 5 mm×5 mm or smaller, for example. In some embodiment, for example, the set of miniature lenses 221 have aperture sizes between about 0.8 mm and 1.5 mm while the first and second relay lenses 205, 209 have aperture sizes of about 20 mm, for example between about 30 mm and 10 mm or 25 mm and 15 mm in some embodiments. The optical imaging system may gather light reflected from the posterior segment or more specifically the retina 201 of the eye. The light passes through the center of the iris opening and the crystalline lens of the eye, and forms a real image (of the posterior segment or retina) at the secondary image plane 208. As discussed above, the imaging lens 104 may include single or multiple lenses, with spherical or non-spherical surfaces. In some embodiments, the secondary image plane 208 is located near the back focal plane of lens 205. In some embodiments, a relay lens 209 may be used to project the image from the secondary image plane 208 to infinity when the front focal plane of the lens 209 is also placed near the secondary image plane 208. A miniature image sensor 220, either in form of CCD, CMOS or other types, with its own miniature lenses 221, may be positioned near the back focal plane of the lens 209 along the optical axis of the optical imaging system. The miniature lenses 221 may include multiple optical lenses. In some embodiments, the image sensor 220 has an active area that is about 6.2 mm×4.6 mm or, for example, between about 8 mm and 4 mm×6 mm and 3 mm or between about 7 mm and 5 mm×5 mm and 4 mm. Accordingly, in various embodiments the active areas of the sensor 210 are about ¼ of the aperture size of the relay lenses 205, 209 or for example between about 0.4 and 0.2 or 0.5 and 0.1 the size thereof. The diagonal of the sensor 210 are also about 1.4 times of focal length of the miniature lenses 211 or, for example, between about 1.6 and 0.8 times of the focal length.

In some embodiments, the optical imaging system has an aperture that is disposed in the set of miniature lenses 221. FIG. 2, for example, shows the aperture 211 positioned between lenses comprising the set of miniature lenses 221 and in front of the miniature image sensor 220. In some embodiments, the aperture 211 of the optical imaging system is positioned in front of the set of miniature lenses 221. In some such embodiments the aperture 211 is disposed between the miniature lenses 221 and the relay lens 209, however, possibly closer to the miniature lenses. Because the designed object plane for the miniature lenses 221 is at infinity, the use of such miniature lenses may bring the retinal image from the infinity to the image sensor 220. In various embodiments, the miniature lenses 221 are built with a circular optical aperture (iris) 211, which may be located between miniature lenses in the set of miniature lenses or formed by an aperture plate in front of the miniature lenses 221. In certain embodiments such location of the iris 211 reduces optical aberration. The miniature lenses 221 may not only relay the image of the retina 201 to the image sensor 220, but also form an entrance pupil for the optical imaging system near the surface of crystalline lens when the aperture 211 becomes the aperture of the entire optical imaging system. This special arrangement helps to eliminate significant amount of scattering light from the anterior chamber of the eye and the optical elements in the optical imaging system.

FIG. 2, as do other drawings, show example optical designs. Accordingly, the number of lens element or optical components, for example, in each lens as well as their shapes, locations, configurations, and arrangement may vary. For example, although the first relay lens 205 is shown in FIG. 2 as a cemented doublet and with one concave and one convex outer surface, this relay lens may comprise a group of lenses including one cemented doublet and one air spaced singlet. In various embodiments, however, one or more optical elements are included that provide the function of a relay lens such as the relay lens 205.

FIG. 3 schematically illustrates a light conditioning element 506 employed in various embodiments of the eye imaging apparatus. To obtain high quality images, proper illumination is provided through the proper portion of the natural opening of the eye while avoiding the imaging path. In particular, illumination is provided through the peripheral regions of the eye pupil. This approach reduces backscatter from the central portions of the pupil, which would degrade the image of the retina obtained by light reflected from the retina also passing through the pupil. Since the eye is a complicated biological organ with its own special optical systems, the scattering and reflection from the eye in combination with its small aperture cause significant difficulties in obtaining a high quality image. In particular, the reflection and scattering from the eye cause glare and haze, which obscures the images acquired by an eye imaging apparatus. Thus the images from the posterior segment of the eye with a wide field of view often exhibit a layer of strong haze or glare. This problem is especially acute for the patients with dark pigmentation in the eyes. Providing illumination through certain regions of the eye as described herein, however, can reduce this backscatter and reflection and the resultant haze and glare.

In various embodiments, a light conditioning element 506 with a multi-segment surface 541 can be configured to receive light from the light source and direct light to the eye in an illumination pattern that, in various embodiments provide for illumination of peripheral sections of the retina. In some embodiments, the light conditioning element 506 splits the light from the light source into different portions by reflection (e.g. total internal reflection) from and/or refraction caused by the multi-segment surface. The light conditioning element 506 may be configured to direct a first portion of light from an inner edge 511 of the light channel 530 to a central area of a retina near an optical axis of the eye imaging apparatus, and direct a second portion of light from an outer edge 509 of the light channel 530 to a peripheral area of the retina away from the optical axis. To overcome the problems of scattering from the cornea and the anterior surface of the crystalline lens, the light conditioning element 506 with a multi-segment surface 541 may be configured to direct the light such that the light primarily falls outside the imaging path of the optical imaging system at the cornea and the anterior surface of a crystalline lens of the eye.

As shown in FIG. 2, the eye imaging apparatus 100 can comprise plurality of light emitting elements 223 as the light sources. The light source of the eye imaging apparatus may emit light in the visible spectrum, IR spectrum, near IR spectrum and/or UV spectrum. The light emitting elements 223 may include solid state light emitters such as light emitting diodes and/or any other elements that are capable of emitting light. The light emitting elements may be compact, highly efficient and driven by low voltage. The light sources 223 may be placed directly against the light conditioning element 222. The light sources 223 may include the light emitting elements and the heat sink which is used to disperse the heat generated by the solid state emitting devices. The light from the light sources is directed into the posterior segment of the eye through the light conditioning element 222 and optical window 102.

In various embodiments, the location of the light sources may be distributed evenly to provide uniform illumination on the retina. The number of the light sources may vary, depending for example on the particular application. FIG. 4 and FIG. 5 schematically illustrate two embodiments of the distribution of the light emitting elements, where a total of 8 and 4 light emitting elements, respectively, are used. In one embodiment, the light emitting elements 902 is mounted onto a heat sink 901 that comprises a ring to increase its mass and heat dispersion capability. There are 8 light emitting elements 902 spaced evenly on the heat sink. The light emitting elements may be activated sequentially or simultaneously or be activated in any desired order. In various embodiments, the light emitting elements are also synchronized with the shutter of the image sensor. Drivers and/or a controller can be employed to control the timing of and/or sequence of illumination. Although 4 and 8 light emitters are shown in FIG. 4 and FIG. 5, more or less number of light emitting elements may be used. In some embodiments, sufficiently large numbers of emitters are employed such that the light sources form a "linear" line source. Such a "linear" line source may be curved and may form a ring centered about the optical axis of the imaging system, for example, in some embodiment. FIG. 5 shows an embodiment with 4 light emitting devices 904, 905, 906, 907 at 0°, 90°, 180°, and 270° positioned on an annular heat sink 903.

An eye imaging apparatus with a wide field of view that employs sequential illumination as described herein is capable of overcoming scattering problems, and thus obtaining high quality images that are essentially glare or haze free. In some embodiments, the eye imaging apparatus comprises a light source disposed inside the housing wherein the light source comprises a plurality of light emitting elements configured to illuminate different portions of an eye time-sequentially. The image sensor is configured to receive a plurality of images of the eye with a same wide field of view through the optical imaging system while each portion of the eye is illuminated time-sequentially. In some embodiments, the eye imaging apparatus further comprises a memory configured to temporarily store the plurality of images, and a computing and communication unit configured to receive and transmit the plurality of images.

In various embodiments, the plurality of images may be transferred to other computing devices or internet based devices that include an image processing unit, which is configured to generate a set of instructions to process the plurality of images to create a single clear image. In some other embodiments, the eye imaging apparatus further comprises an image processing unit configured to generate a set of instructions to process the plurality of images to create a single clear image of the eye.

Figure 6:
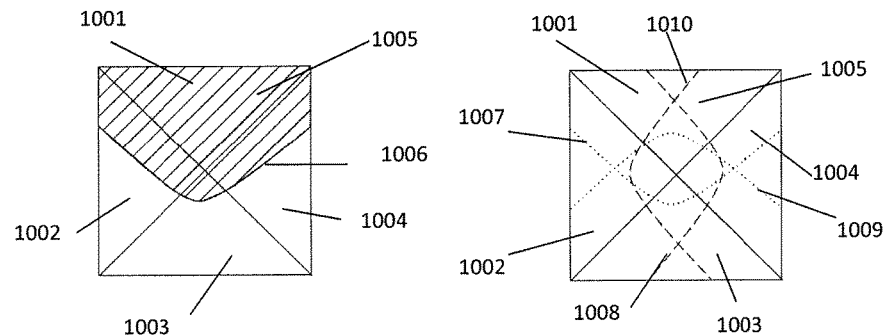
FIG. 6 schematically illustrates the images acquired when the light emitting elements are activated time-sequentially and a sequential illumination method used to enhance image quality according to various embodiments of the invention.

FIG. 6 schematically illustrates the example images acquired when the light emitting elements are activated time-sequentially and the method used to enhance the image quality according to various embodiments of the invention. A useful illumination condition is created when the light emitting elements are activated time-sequentially. For example, in an illumination system with 4 light emitting elements, if only one light emitting element is activated, then a first portion of the retina or the posterior segment of eye has increased illumination in comparison to other portions of the retina or posterior segment of the eye. At a later time if a second light emitting element is activated, a second portion of the retina or the posterior segment of eye has increased illumination in comparison to other portions of the retina or posterior segment of the eye including the first portion. Likewise at a later time if a third light emitting element is activated, a third portion of the retina or the posterior segment of eye has increased illumination in comparison to other portions of the retina or posterior segment of the eye including the first and second portions. Again, at a later time if a fourth light emitting element is activated, a fourth portion of the retina or the posterior segment of eye has increased illumination in comparison to other portions of the retina or posterior segment of the eye including the first, second, and third portions. In this example, where the retina is divided into four such sections, each of the four portions may be about 25% of the retina. However, in other embodiments the portion with increased illumination may be less than 50%, 40% or 30% but larger than 1%, 2%, 5%, 10% or 20% of the eye. In some embodiments, this portion is between 20-30%. Other values outside these ranges are also possible.

In various embodiments, this portion is on average illuminated more than other portions of the eye and has an average intensity greater than that of remaining portion or portions of the retina or posterior segment of the eye. Accordingly, only a portion of the example image 1001 acquired by the eye image apparatus is shown as having increased illumination in FIG. 6. In the example image 1001, the shaded area which is a bit larger than one quarter 1005 of the image has increased illuminated, while on average remaining quarters 1002, 1003 and 1004 are as well illuminated less. However, due to the unique scattering characteristic of the eye, the scattered light by the eye may show up mostly in the oppositely situated quarter 1003 in the form of haze or glare, leaving a clear portion in the primarily illuminated quarter 1005. The clear portion is essentially glare or haze free, or only has negligible glare or haze. Accordingly the quarter 1005, the clear portion, has substantially less glare or haze than the other portion. The brightness of the illuminated area often gradually decreases toward its boundary area 1006, while the brightness of image in the quarter 1005 is relatively uniform and with proper light exposure for the image sensor.

Accordingly, in various embodiments, the first portion (approximately a quarter) 1005 of the retina or posterior segment is illuminated, for example, by providing light from one of the light emitting elements while the other light emitters remain unactivated. Subsequently, another one of the light emitting elements is activated. As the next light emitting element is activated, the illuminated area is moved to be centered on another portion such as another quarter 1002 of the retina or posterior segment. Another image is captured. Next a third portion, for example, quarter 1003 is illuminated by activating another of the light emitting elements. Finally, a fourth portion or quarter 1004 is illuminated by activating another of the light emitters and another image is capture. In such an example, each of the emitters is activated while the others remain inactivated. When all of the 4 light emitting elements are activated time-sequentially, 4 images with different quarters having increased brightness and clear portions are acquired.

The order of sequence can vary. Additionally, although activation of only one emitter at a time was discussed above, in certain embodiments, two are more light emitters are activated during the same time period. Additionally, although an image can be captured each time a different light source is activated, more than one image may also be recorded. Also, activating the light emitting element may comprise switching the light emitter on as compared to being off or otherwise increasing optical output therefrom for example significantly.

Additionally, the light from the light emitting elements may be blocked, impeded, attenuated or redirected or otherwise modulated. In various embodiments, however, different portions of the retina or posterior segment are selectively illuminated more than other portions. The portion selected for increased illumination can be changed so as to provide increased illumination of the different portions at different times. Such selective illumination can be synchronized with the images captured at those times. Accordingly, images can be obtained at these different times and used to produce a composite image that has less haze and glare. In some embodiments, a driver and/or controller is used to activate the light emitters, direct light from a selected emitter or emitters and not from the others or otherwise selectively modulate the emitters. In some embodiments, simply more light from the selected emitter or emitters is provided in comparison to the other emitter. In certain embodiments shutters, light valves, and/or spatial light modulators are employed to control the amount of light from each of the light emitting elements. Although one emitter at a time was describe above as being activated, more than one light emitter can be activated at a time. In various embodiments, more light is provided by a subset of the total number of emitters so as to illuminate a portion of the retina or posterior segment or illuminate that portion more than one or more other portions. An image is recorded. Subsequently, a different subset of the total number of emitters is selected to illuminate another portion of the retina or posterior segment or illuminate that portion more than others. Another image is recorded. This process can be repeated multiple times in various embodiments. For example, 2, 3, 4 or more subsets may be selected at different times or for providing the primary illumination. Images of the eye may be obtained at the different times. These images or at least portions of these images may be employed to form a composite image of the eye, for example, of the retina and/or posterior segment. Accordingly, in various embodiments an imaging processing unit may be configured to generate a set of instructions to process the plurality of images to create a single clear image of the eye. Because the eye or the eye imaging apparatus may be moved slightly during the image capturing or imaging process, the plurality of images may not overlap precisely. The imaging processing unit may generate instructions to precisely align the plurality of images or portions thereof by analyzing the overlapping areas. Each of the plurality of images has a clear portion and an unclear portion. The clear portion of the image is essentially glare free or haze free, or has negligible glare or haze. The clear portion has substantially less glare or haze than the other portion, the unclear portion. The unclear portion exhibits glare or haze, which obscures the image. The imaging processing unit may further generate instructions to recognize the clear portion of an image in each of the plurality of images, remove an unclear portion and save the clear portion. The set of instructions may further include instructions to adjust the uniformity of the image brightness of the single clear picture near a border area to form a uniform brightness. The imaging processing unit is configured to combine the plurality of images to create the single clear image.

As shown in the example image 1001 in FIG. 6, for example, in an illumination system with 4 light emitting elements, when the quarter 1005 is well illuminated, the unclear portion of the image with glare is outside the boundary 1007. The unclear portion may be recognized and removed by a set of instructions from an image processing unit. Therefore only the clear portion of the image within the boundary 1007 is saved. Similarly, only the clear portion of the image within the boundary 1008 is saved when the quarter 1002 is well illuminated. Two additional images are acquired from the quarter 1003, 1004 and their surrounding areas which are within the boundaries 1009 and 1010, respectively. When all of the 4 light emitting elements are activated time-sequentially, 4 partial images are acquired.

Because the eye or the eye imaging apparatus may be moved slightly during the imaging process, the features from the 4 partial images may not overlap precisely. In some embodiments, the extended area from the border of each quarter may be used to allow the proper adjustment and re-alignment of the images as set forth by the instructions from the imaging processing unit. After the 4 images are aligned precisely, the brightness of the images in the border area can be re-adjusted to produce one single clear image with uniform brightness.

In some embodiments, in order to align the images taken time sequentially, one or more additional images may be captured with all of the light emitting elements activated at the same time, in addition to the multiple images taken time-sequentially as described above. This image can be obtained using the same optical imaging system having the same field of view as was used to obtain the plurality of images obtained with time-sequential illumination. Although such image may be hazy or with glare, it may contain the unique graphic reference features, such as blood vessels, of the whole imaging area or the entire field of view. Using this image as a reference image to coordinate, each of the four partial images described above may be aligned with the reference image. The clear composite image could then be formed from the four images after proper adjustment of the locations.

Although in the example embodiment described above, a single reference image was obtained with all the light emitters activated to assist in alignment of the other images, in other embodiments less than all light emitters may be illuminated. For example, the light emitters for two quarters 1002, 1003 can be activated to align those quarters. Similarly, the light emitters for the other quarters 1004, 1005 can be activated to align those quarters. Additional images with less than all the light emitters can be activated to provide further alignment. For example, four reference images captured while illuminating different pairs of the four quarters may be used to align each of the four quarters and create a complete composite image.

Less reference images can also be used, for example, by illuminating more sections when capturing the reference image. In some embodiments, for example, a first reference image can be captured with three of the four quarters illuminated, and a second reference images can be captured with different three of the four quarters illuminated. Alignment can be provided using these first and second reference images. Other variations are possible. As discussed above, the number of sections illuminated and number of light emitters used to obtain the one or more reference images can vary.

Accordingly, one or more reference image can be employed to align images of sections obtained using time-sequential illumination. To generate a reference image, multiple sections are illuminated and an image is capture by the optical imaging system and sensor. This reference image will depict the sections and their positional relationship, and will contain reference features that can be used to align separate images of the separate sections. Although reference images can be obtained by illuminating all of the sections, not all the sections need to be illuminated at the same time to produce reference images that can assist in alignment. These reference images can be captured using the same optical imaging system having the same field of view as was used to obtain the plurality of images captured during time-sequential illumination. However, in alternative embodiments, reference images can be captured by other optical imaging systems and sensor. Additionally, reference images can be captured with using different fields-of-view. Other variations are possible.

An image processing unit may be utilized to process the images as set forth above to provide alignment. For example, the image processing unit may identify the reference features in the reference images to determine the positional relationship of the sections. The image processing unit may further align sections of images captured using time sequential illumination based on those reference features and the determined positional relationship of the sections.

In various embodiments, the rate of frequency of the time-sequential capturing is determined by the image capturing rate. In some embodiments, the imaging apparatus is configured to capture each image between 15 ms or 30 ms to 150 ms or 200 ms.

Accordingly, a method of imaging an eye by sequential illumination is disclosed to obtain high quality retinal images with a wide field of view. The method comprises activating a plurality of light emitting elements time-sequentially to illuminate different portions of an eye, imaging the eye through an optical imaging system and receiving a plurality of images of the eye through the optical imaging system and sensor while different portions of the eye are illuminated time-sequentially. The images are captured by the image sensor and processed to create a single clear image of the eye. The method may be used to digitally remove the unclear sections, thus reducing or removing the haze from the plurality of images obtained from the sequential illumination.

The sequential illumination method discussed in the previous paragraph may be applied when different numbers of the light emitting elements are used. The possible examples include 2 elements, 3 elements, 4 elements, 6 elements, 8 elements or even more elements. The light emitting elements need not be individually activated. In some embodiment, pairs may be activated at a time. Similarly, 3, 4, or more may be activated at a time. Other variations are possible.

Accordingly various embodiments comprise an eye imaging system comprising an eye imaging apparatus such as for example shown in FIG. 1(A) and FIG. 1(B), and an image computing apparatus that includes another computing device or internet based device. The eye imaging apparatus may comprise a plurality of light emitting elements, an optical imaging system, an image sensor, memory and a computing and communication unit. In certain embodiments, the plurality of light emitting elements is configured to illuminate different portions of an eye time-sequentially. The image sensor is configured to receive a plurality of images of the eye with a same wide field of view through the optical imaging system as the different portions of the eye are illuminated time-sequentially. In various, although not all embodiments, the memory is configured to at least temporarily store the plurality of images captured by the image sensor. The computing and communication unit may be configured to receive and transmit the plurality of images. The eye imaging apparatus may further include a touch screen display to display the images.

In some embodiments, the image computing apparatus may be configured to receive the plurality of images from and exchange data with the eye imaging apparatus. The communication between the eye imaging apparatus and the image computing apparatus may be wireless. The image computing apparatus may further include an image processing unit, which is configured to generate a set of instructions to process the plurality of images to create a single composite image of the eye. The image computing apparatus may transmit the composite image to the eye imaging apparatus and display the composite image in the touch screen of the eye imaging apparatus.

In some other embodiments, the eye imaging apparatus may further comprise an image processing unit, which is configured to generate a set of instructions to process the plurality of images to create a single composite image of the eye. The eye imaging apparatus may display the composite image on the touch screen and transmit the composite image to other apparatuses, such as the image computing apparatus, an image display apparatus, or an image storage apparatus. The transmission of the composite image to other apparatuses can be wireless. In some embodiments, the image computing apparatus may be disposed in a carrying case. The carrying case can be configured to hold the eye imaging apparatus, the image computing apparatus, a large image display and other items such as a photo printer simultaneously.

Various embodiments disclosed herein comprise a syntactic image analyzing method to process a plurality of images and compose a single composite image. The syntactic image analyzing method comprises analyzing the plurality of images with a same field of view and combing the plurality of images into the single composite image. The plurality of images can comprise 2 images, 3 images, 4 images, 6 images, 8 images, 10 images, 12 images, 20 images, 100 images or any other number of images. In conventional image stitching, for example, combing a plurality of images to produce a panorama image, the plurality of images can be captured with different fields of view and under almost the same distribution of illumination light intensity. In syntactic image analyzing, unlike in conventional image stitching, the plurality of images can be captured with a same field of view, but under different distribution of illumination light intensity. For example, the plurality of images can be taken under the sequential illumination discussed above. Each of the plurality of images can be from the same portion of the eye, but include different information resulting from the different illumination conditions. Moreover, in conventional image stitching, the plurality of images can be stitched together to form a larger image. But in syntactic image analyzing, the plurality of images can be combined to form a single composite image with a same size of each of the plurality of images, but providing more detailed information than each of the plurality of images. Unlike conventional image stitching, the plurality of images captured under sequential illumination cannot be simply stitched together. Each of the plurality of images under sequential illumination can have a clear portion which can be substantially haze or glare free and an unclear portion which can have haze or glare. In terms of position, each image is essentially superimposed to another image. In other words, each image can be essentially with the same field of view at the same position. However, both the operator and the eye imaging apparatus can move slightly during then imaging procedure, the plurality of images can have slight misalignment. But if simply aligning and combing the plurality of images, the clear portion of one image can be obscured by the unclear portions of the other images, thus defeating the purpose of sequential illumination. Therefore, each of the plurality of images needs to be analyzed before aligning and combing the plurality of images. Because of the distinct characteristics of the plurality of images under sequential illumination, the syntactic image analyzing method can be used to analyze each of the plurality of images including identifying the clear portion and removing or filtering out the unclear portion. Then, the syntactic image analyzing method can further align and combine the plurality of images into a single clear composite image. The composite image can be essentially or substantially free of haze or glare for the entire field of view, providing detailed information with high resolution for diagnosis and treatment purpose.

Figure 7:
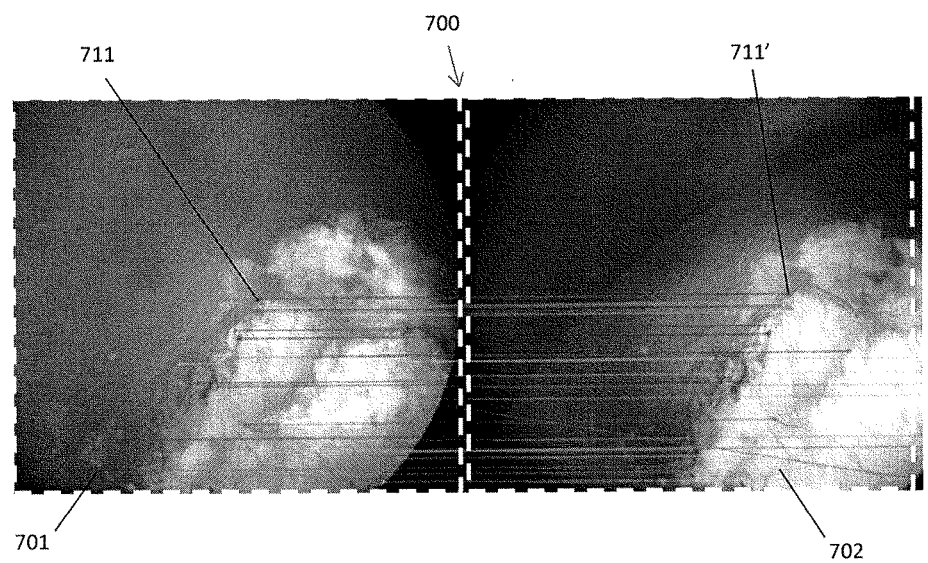
FIG. 7 schematically illustrates the syntactic image analyzing method 700 which comprises identifying landmarks or reference points in the plurality of images.

FIG. 7 schematically illustrates the syntactic image analyzing method 700 which comprises identifying landmarks or reference points in the plurality of images. The landmarks or reference points are distinct detection features in the plurality of images. The reference points can be a set of special points that can be identified and used to align the plurality of images. The optic disc and the fovea can be the potential reference points. Moreover, the intersections of blood vessel or nerves of the posterior segment can also be recognized as the reference points. FIG. 7 illustrates some of the reference points in aligning two images of the posterior segment of the eye, the first image 701 and the second image 702. For example, the reference point 711 can be identified in the first image 701, and the corresponding reference point 711' can be identified in the second image 702.

In some embodiments, the syntactic image analyzing method 700 can comprise identifying the reference points by using Scale-invariant feature transform (SIFT) feature detector combined with Brute Force Matcher. In some other embodiments, the syntactic image analyzing method 700 can comprise identifying the reference points by using Harris feature detector. In some alternative embodiments, the syntactic image analyzing method 700 can comprise other algorithms identifying reference points by tracking the intersections of blood vessels, nerve head, and other features.

It can be important to find a set of appropriate parameters to be used to identify the reference points. The set of appropriate parameters can affect the quality of the reference points. The set of appropriate parameters can also affect other aspects of the syntactic image analyzing method 700, such as speed, accuracy, flexibility, etc. In some embodiments, the syntactic image analyzing method 700 can further comprise a machine learning algorithm configured to search the reference points from a large volume of images and determine the set of optimized parameters to be used to identify the reference points.

Figures 8A, 8B:
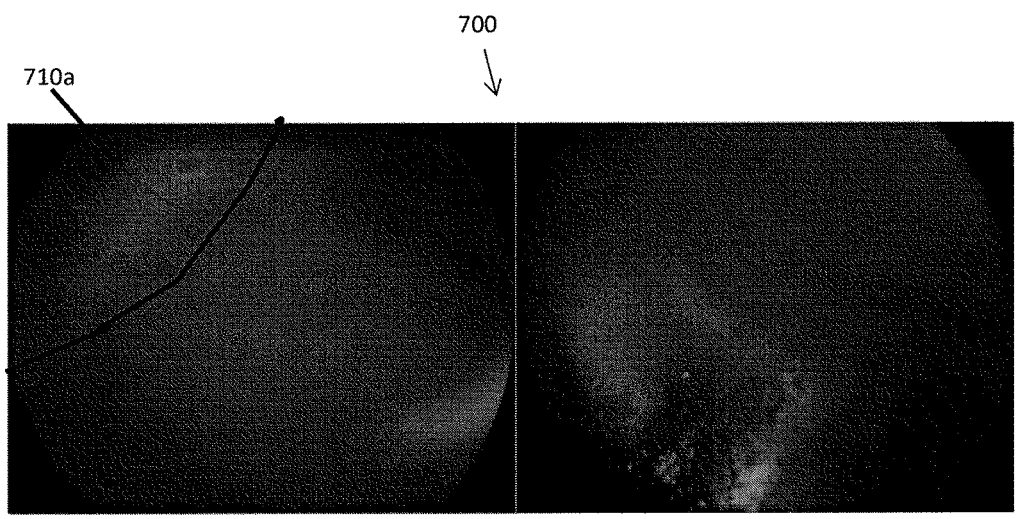
FIG. 8A illustrates the first image acquired under sequential illumination when the first LED light source is activated.
FIG. 8B illustrates the second image acquired under sequential illumination when the second LED light source is activated.
Figures 8C, 8D:
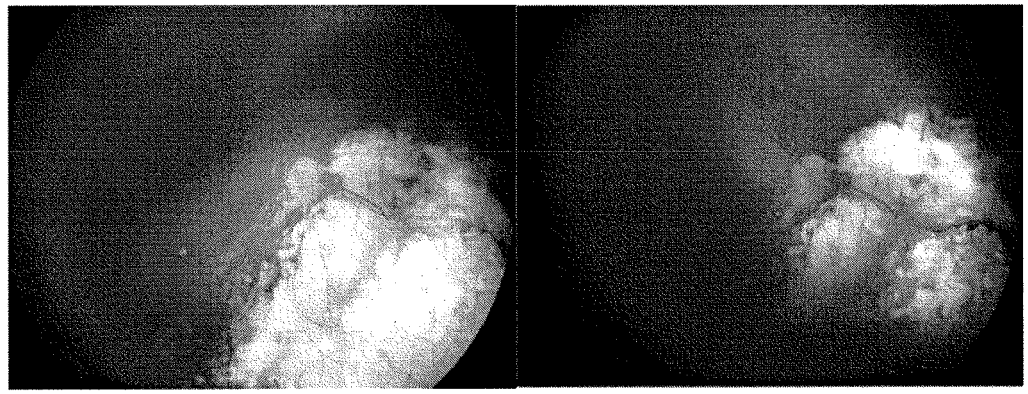
FIG. 8C illustrates the third image acquired under sequential illumination when the third LED light source is activated.
FIG. 8D illustrates the fourth image acquired under sequential illumination when the fourth LED light source is activated.
Figures 8E, 8F:
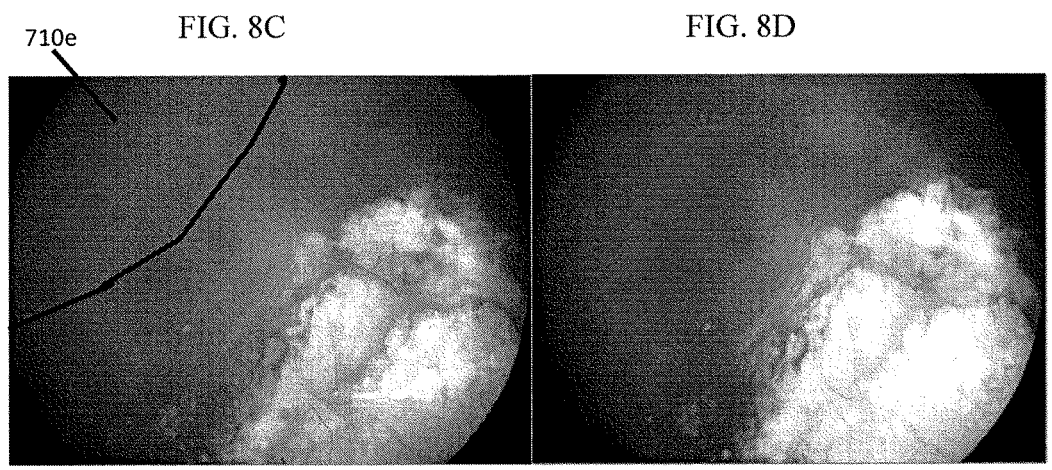
FIG. 8E illustrates the reference image acquired when all LED light sources are activated simultaneously.
FIG. 8F illustrates the single clear composite image obtained by using the syntactic image analyzing method.

FIGS. 8A-8D illustrate the first, the second, the third and the fourth image acquired under sequential illumination when 4 LED light sources are activated sequentially, respectively. FIG. 8E illustrates the reference image acquired when all LED light sources are activated simultaneously. FIG. 8F illustrates the single clear composite image obtained by using the syntactic image analyzing method 700 after color calibration.

The syntactic image analyzing method 700 can comprise analyzing each of the plurality of images to identify a clear portion in each of the plurality of images. As discussed above, because of the special structure of the eye, the images from the posterior segment of the eye often exhibit a layer of strong haze or glare. Under sequential illumination, a plurality of images with different portions having increased brightness and clear portions can be acquired. As discussed above, the clear portions of the plurality of images can be essentially glare free or haze free, or have negligible glare or haze. The clear portions can have substantially less glare or haze than the other portion, the unclear portion. The unclear portions can exhibit glare or haze, which can obscure the images. For example, FIG. 8A illustrates the first image acquired under sequential illumination when the first LED light source is activated. As shown in FIG. 8A, the first image has a clear portion 710a, which can be essentially glare free or haze free, or have negligible glare or haze, thus exhibiting more details about the structure of the retina than the rest of the first image. The rest of the first image is the unclear portion, which has substantially more glare or haze than the clear portion 710a. The glare or haze can obscure the image. Similarly, FIG. 8B-8D illustrates the clear portions in the second, the third and the fourth image when the second, the third and the fourth LED light source is activated respectively. For comparison, FIG. 8E illustrates the reference image acquired without using the sequential illumination method. In other words, the reference image is acquired when all LED light sources are activated simultaneously. The reference image demonstrates more haze or glare compared to the clear portions in the plurality of images acquired under sequential illumination. For example, the clear portion 710a in the first image in FIG. 8A has substantially less glare or haze and provide more detailed structure information than the corresponding portion 710e in the reference image in FIG. 8E.

Figure 9A:
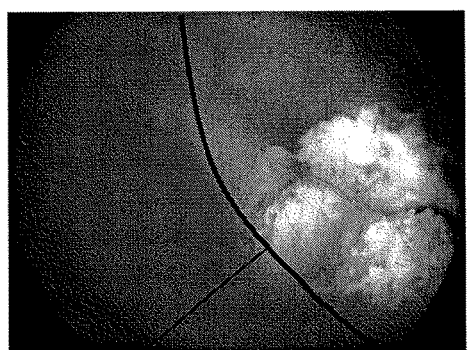
FIG. 9A schematically illustrates the syntactic image analyzing method which comprises analyzing each of the plurality of images and identifying a boundary line according to some embodiments of the disclosure.
Figure 9B:
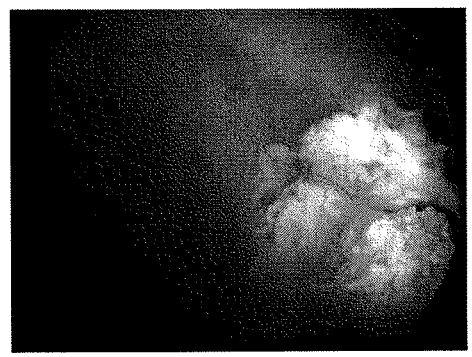
FIG. 9B schematically illustrates the syntactic image analyzing method which comprises analyzing each of the plurality of images and gradually removing an unclear portion according to some embodiments of the disclosure.

FIG. 9A and FIG. 9B schematically illustrate the syntactic image analyzing method 700 which comprises analyzing each of the plurality of images according to some embodiments of the disclosure. The syntactic image analyzing method 700 can include identifying a boundary of a clear portion and gradually removing an unclear portion. The syntactic image analyzing method 700 can identify the clear portions, which are needed by the final composite image, by determining the boundary line of the clear portion in each image. In some embodiments, the syntactic image analyzing method 700 can identify the boundary based on calculation of brightness of the pixels from the optical design of the eye imaging apparatus. The method can determine a first sample area with the pixels of high brightness and a second sample area of pixels with the low brightness. The first sample area can be chosen at the area where the predicted brightness is the highest from the optical design, for example, the center of each quarter in each image. The second sample area can be chosen at the corresponding diagonal symmetric position in the same image. The first and the second sample area can be square, circular, elliptical or any other shapes. The areas of the first and the second sample area can be any reasonable size. For example, the sizes of the first and the second sample area can be 1%, 5%, 10%, 15%, 20%, 50%, 80%, 100% of a quarter of the image or any value there between. The first and the second sample area can include 4 pixels, 8 pixels, 16 pixels, 25 pixels, 36 pixels, 64 pixels, 100 pixels, or any other number of pixels. The method can further decide the boundary line by using the results of the first average brightness of the first sample area and the second average brightness of the second sample area. In some embodiments, the mean brightness of the boundary line can be set to the average of the first average brightness and the second average brightness. In some other embodiments, the mean brightness of the boundary line can be set by weighing the first average brightness and the second average brightness. For example, the mean brightness of the boundary line can be set as the brightness calculated by adding 30% to 70% of the first average brightness with 70% to 30% of the second average brightness.

The method 700 can further comprise identifying a boundary line by finding the pixels with brightness near the mean brightness of the boundary. For example, the method 700 can find the pixels with brightness within from 0% to 30% of the mean brightness of the boundary. The method 700 can further analyze a dataset including the pixels with brightness near the mean brightness of the boundary and find the optimal line fitting results. The method 700 can comprise analyzing distribution and trend of the pixels with brightness near the mean brightness of the boundary. The method 700 can comprise using an iterative sampling process to find the optimal line fitting results and removing the outliers in the dataset. FIG. 9A schematically illustrates a boundary line 930 of a clear portion in the image identified by the syntactic analyzing method 700. The boundary line 930 can be a straight line or a curved line. However, the boundary cannot be a closed line. If the identified line is closed line, which indicates it might be possible some pathologies such tumors resulting in a false "boundary line". If this happens, the false "boundary line" need to be deleted, a new boundary line need to be set that can include the area where the false "boundary line" occurs.

The method 700 can further comprise removing the unclear portion and adjusting a border. After identifying the boundary line 930 as shown in FIG. 9A, the method 700 can further comprise gradually decreasing the brightness of the pixels near the boundary. In some embodiments, the brightness of the pixels near the boundary and away from the clear portion can be exponentially decreased to zero, which can remove the unclear portion with a smooth border. The exponential curve can be used to save sufficient information while information eliminating efficiently. In some other embodiments, the brightness of the pixels near the boundary on the outside away from the clear portion can be gradually decreased to zero linearly, in a parabolic shape, or in some other ways. FIG. 9B schematically illustrates the image after the brightness of the pixels near the boundary away from the clear portion has been exponentially decreased to zero. As in FIG. 9B, there is no obvious boundary shown after the unclear portion has been gradually removed.

In some other embodiments, the syntactic image analyzing method 700 can identify the boundary based on calculation of brightness of the pixels from analyzing the image. For example, the method 700 can determine the pixel with the highest brightness and chose a first sample area around the pixel with the highest brightness. The first sample area can be chosen at the area where the measured brightness is the highest. The second sample area can be chosen at the corresponding diagonal symmetric position in the same image. The areas of the first and the second sample area can be any reasonable size and any reasonable shape. The method can further decide the boundary line by determining the mean brightness of the boundary using the results of the first average brightness of the first sample area and the second average brightness of the second sample area. The method 700 can further comprise identifying a boundary line by finding the pixels with brightness near the mean brightness of the boundary. The method 700 can further find the optimal line fitting results by using an iterative sampling process and removing the outliers in the dataset. As discussed above, the boundary cannot be a closed line, which indicates it might be possible that some pathologies such as tumors can result in a false "boundary line". The false "boundary line" needs to be deleted, and a new boundary line needs to be set that can include the area where the false "boundary line" occurs.

In some alternative embodiments, the syntactic image analyzing method 700 can identify the boundary based on identification of reference points in each image. For example, the first sample area can be chosen at the area which has the most number of reference points. The second sample area can be chosen at the corresponding diagonal symmetric position in the same image. The areas of the first and the second sample area can be any reasonable size and any reasonable shape. The method can further decide the boundary line by determining the mean brightness of the boundary as discussed above. The method 700 can further comprise identifying a boundary line by finding the pixels with brightness near the mean brightness of the boundary. The method 700 can further identify the boundary line by finding the optimal line fitting results. However, it is possible that some pathologies may obscure the number of reference points detectable and result in a false "boundary line". The false "boundary line" needs to be deleted, and a new boundary line needs to be set.

Figure 10:
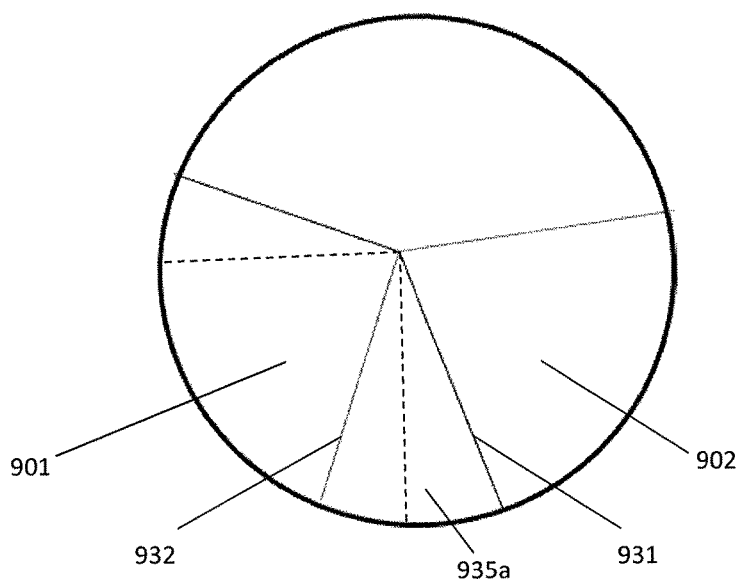
FIG. 10 schematically illustrates some other embodiments of the syntactic image analyzing method.

FIG. 10 schematically illustrates some other embodiments of the syntactic image analyzing method 700. The syntactic image analyzing method 700 can determine a boundary of a clear portion as a line enclosed in an area that is larger than a quarter of the image. For example, the line 931 can be the boundary line for the clear portion in image 901 and the line 932 can be the boundary line for the clear portion in image 902. The boundary line can enclose an area that is 5%, 10%, 15%, 20%, 25%, 30% of the size of a quarter of the image or any values there between. The method 700 can further comprise adjusting the border by gradually decreasing the brightness of the pixels in area 935a inside the boundary in image 901 in some embodiments. The method 700 can further comprise adjusting the border by gradually decreasing the brightness of the pixels outside the boundary in image 901 in some other embodiments.

Figure 11:
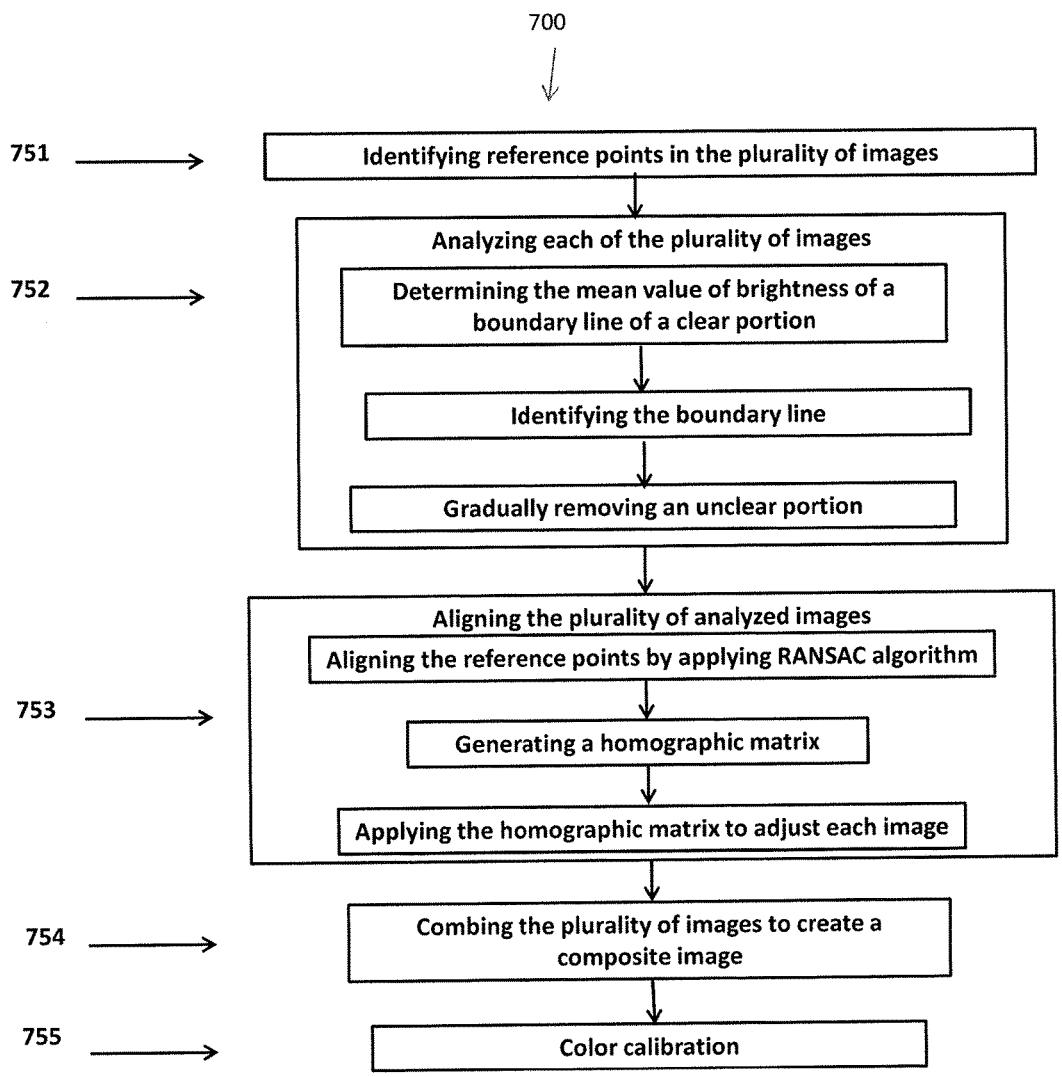
FIG. 11 schematically illustrates a flow diagram of the syntactic image analyzing method.

FIG. 11 schematically illustrates a flow diagram of the syntactic image analyzing method 700. The syntactic image analyzing method 700 can comprise identifying reference points in the plurality of images acquired under sequential illumination, as shown in block 751. In some embodiments, the method 700 can further comprise identifying reference points in a reference image which is acquired without sequential illumination. The method can further comprise analyzing each of the plurality of images acquired under sequential illumination one by one as shown in block 752. The method 700 can be configured to identify a clear portion and a boundary line between the clear portion and an unclear portion. In some embodiments, the method 700 can comprise determining a first sample area and a second sample area, and calculating the first average brightness of the first sample area and the second average brightness of the second sample area as discussed above. The method 700 can further comprise determining the mean value of brightness of the boundary line by using the combination of the first average brightness and the second average brightness. The method 700 can further comprise identifying the boundary by finding the optimal line fitting based on the mean value of brightness of the boundary line. In order to create a seamless transition, the method 700 can further comprise gradually removing the unclear portion by gradually decreasing the brightness of the pixels near the boundary away from the clear portion to zero. The method 700 can comprise analyzing each of the plurality of images and gradually filtering out the unclear portion.

As shown in block 753 of FIG. 11, the syntactic image analyzing method 700 can comprise aligning the plurality of images based on reference points. In some embodiments, the method 700 can comprise aligning the reference points in each of the plurality of images to the reference points in the reference image. In some embodiments, the method 700 can align the reference points in each of the plurality of images to the adjacent image of the plurality of images. The method 700 can comprise aligning the reference points by applying Random sample consensus (RANSAC), which is an iterative method to estimate parameters from the reference points to remove the outlier reference points. The method 700 can comprise generating a homographic matrix for image registration. The homographic matrix can be 2D matrix. The homographic matrix can be generated by RANSAC. The homographic matrix can be used to adjust the set of reference points in one image to align with another image. The method can further comprise applying the homographic matrix to adjust each image to align the plurality of images.

The method 700 can comprise aligning the plurality of images using the reference points and preventing the composite image from distortion and cracking. In some embodiments, the method 700 can comprise establishing a coordinate system with the reference points which can be used to determine the positions of other images of the plurality of images. Then, according to the calibration of the positions, all images can be adjusted to fit the appropriate position for the further composition. In some embodiments, the method 700 can comprise correcting distortion and misalignment of identified reference points. This method 700 can comprise identifying any matching points that can be used to confirm the positions of the pixels of the plurality of images based on the identified reference points. According to the positions of pixels of the reference points, the method 700 can comprise adjusting the plurality of images pixel by pixel till all pixels in the plurality of images fit the corresponding positions.

The syntactic image analyzing method 700 can comprise composing a single clear composite image by combining the plurality of images. In some embodiments, the method 700 can further comprise blending at the overlapping areas of the plurality of images. The method can comprise blending the pixels by weighing the pixels of the two images which are overlapped, for example, one image can have a larger weight than the other image in some embodiments. In some other embodiments, the pixels at the overlapping area can be blended by averaging the pixels from the two overlapped images. In some alternative embodiments, the method 700 can comprise selecting the pixels with higher brightness from the two overlapped images in order to improve speed.

The syntactic image analyzing method 700 can comprise color calibration of the single clear composite image after combining the plurality of images. Because of the nature of the image sensor, the color of the composite image can be calibrated to be real color to assist in the correct diagnosis of the various eye diseases. In some embodiments, the method 700 can comprise capturing an image of a gray card by the eye imaging apparatus with uniform brightness after adjusting the white balance parameter of the eye imaging apparatus. The image of the gray card can be captured under the same illumination conditions of the imaging system, however, the eye imaging apparatus can be defocused such that the light distribution can be as uniform as possible. The method can further comprise calculating the corrected parameters out from the captured image, then applying the corrected parameters to calibrate the color of the composite image to achieve the best result. As shown in FIG. 8F, the single clear composite image obtained by using the syntactic image analyzing method 700 after color calibration is warmer in color than the plurality of images without color calibration.

In some embodiments, the syntactic image analyzing method 700 can comprise aligning the reference points in each of the plurality of images to the reference points in the reference image, then comparing each of the plurality of images to the reference image to determine the boundary of the clear portion in each image. For example, the pixels in the clear portion of each image can have brightness higher than that of the corresponding pixels in the reference image while the pixels in the unclear portion of each image can have brightness lower than that of the corresponding pixels in the reference image. By comparing the brightness of the pixels in each image to the reference image, the boundary line can be identified when the difference in brightness of the pixels in each image compared to the reference image changes signs from positive to negative. In some other embodiments, can comprise comparing the detectable reference points in each image with the detectable reference points in the reference image. The clear portion of each image can have more number of detectable reference points than the corresponding portion in the reference image while the unclear portion of each image can have less number of detectable reference points than the corresponding portion in the reference image. The method 700 can identify the boundary line when the difference in the number of detectable reference points between each image and the reference image begins to decrease. In some alternative embodiments, the method 700 can compare the brightness of reference points in each image with the brightness of the corresponding reference points in the reference image, and can identify the boundary when the difference approaches zero.

The syntactic imaging analyzing method can have many variations without departure from the scope of the disclosure. The plurality of images can be analyzed and the clear portion in each image can be identified by using various approaches. In some embodiments, the boundary of the clear portion can be identified by detecting the rate of the brightness change in the pixels and the boundary can be determined by finding a line with the highest rate of the brightness change in the pixels. For example, the method 700 can plot a set of lines of pixels with essentially the same brightness while the difference in the brightness between the lines can be constant. The method can then determine the boundary line which can be the line with the shortest distance to the adjacent line. In some other embodiments, the method 700 can comprise analyzing the distribution of the reference points and identifying the boundary line where the number of reference points decrease rate is the highest. In some alternative embodiments, the method 700 can comprise other machine learning and pattern recognition methods to identify the boundary line in each image of the plurality of images. In some embodiments, the method can comprise aligning the plurality of images and combing the plurality of images by selecting the pixel with the highest brightness at the same position among the plurality of images and compose all pixels with the highest brightness in the entire field of view into a single composite image.

Various embodiments disclosed herein comprise a non-transitory, computer-readable storage medium storing a set of instructions capable of being executed by a processor to combine a plurality of images with a same field of view into a composite image. The non-transitory, computer-readable storage medium can be disposed in an image computing apparatus configured to communicate with the eye imaging apparatus in some embodiments. The eye imaging apparatus can be configured to transmit the plurality of images acquired under sequential illumination to the image computing apparatus, and the imaging computing apparatus can be configured to process the plurality of images into the composite image and transmit the composite image to the eye imaging apparatus. The non-transitory, computer-readable storage medium can be disposed in the eye imaging apparatus in some other embodiments. When executed by the processor, the non-transitory, computer-readable storage medium can cause the processor to identify reference points in the plurality of images as well as in the reference image. The non-transitory, computer-readable storage medium can further cause the processor to analyze each of the plurality of images to identify a clear portion and a boundary line between the clear portion and an unclear portion. In some embodiments, non-transitory, computer-readable storage medium can cause the processor to determine a first sample area and a second sample area, and calculate the first average brightness of the first sample area and the second average brightness of the second sample area. The non-transitory, computer-readable storage medium can further cause the processor to determine the mean value of brightness of the boundary line and identify the boundary by finding the optimal line. The non-transitory, computer-readable storage medium can further cause the processor to gradually remove the unclear portion by gradually decreasing the brightness of the pixels near the boundary away from the clear portion to zero.

The non-transitory, computer-readable storage medium can cause the processor to align the plurality of images based on reference points by applying RANSAC algorithm and removing the outlier points. The non-transitory, computer-readable storage medium can further cause the processor to generate a homographic matrix and adjust each image. Moreover, the non-transitory, computer-readable storage medium can cause the processor to compose a single clear composite image by combining the plurality of images. In some embodiments, the storage medium can further cause the processor to perform color calibration.

While the present disclosure has been disclosed in example embodiments, those of ordinary skill in the art will recognize and appreciate that many additions, deletions and modifications to the disclosed embodiments and their variations may be implemented without departing from the scope of the disclosure.

A wide range of variations to those implementations and embodiments described herein are possible. Components and/or features may be added, removed, rearranged, or combinations thereof. Similarly, method steps may be added, removed, and/or reordered.

Likewise various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Accordingly, reference herein to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below.

Additionally as used herein, a phrase referring to "at least one of" a list of items refers to any combination of those items, including single members. As an example, "at least one of: a, b, or c" is intended to cover: a, b, c, a-b, a-c, b-c, and a-b-c.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. An eye imaging apparatus comprising:
   a housing,
   a light source disposed inside the housing comprising a plurality of light emitting elements each configured to illuminate a different portion of an eye time-sequentially, wherein one of the plurality of light emitting elements is configured to be activated at one time to illuminate one portion of the eye, the one portion having a greater average light intensity than other portions, and the one portion is located across an optical axis from the one of the plurality of light emitting elements;
   an optical imaging system having the optical axis and disposed inside the housing comprising an optical window, the optical window having a concave front surface configured to receive a portion of the eye;
   an image sensor disposed inside the housing configured to receive a plurality of images of the eye with a same field of view through the optical imaging system while each portion of the eye is illuminated time-sequentially by one of the light emitting elements; and
   a computing and communication unit disposed inside the housing comprising
      an image processing unit configured to analyze the plurality of images to identify a clear portion in each of the plurality of images by identifying a boundary line of the clear portion and to process the plurality of images into a single composite image, wherein the image processing unit is further configured to adjust the boundary line by gradually decreasing brightness of pixels near the boundary line away from the clear portion in each of the plurality of images;
      a display configured to display the plurality of images and the single composite image; and
      a wireless communication device configured to receive and transmit the plurality of images and the single composite image.

2. The eye imaging apparatus in claim 1, wherein the image processing unit is configured to identify the boundary line by determining a first sample area and a second sample area.

3. The eye imaging apparatus in claim 1, wherein the image processing unit is configured to identify the boundary line by determining brightness of pixels in each of the plurality of images.

4. The eye imaging apparatus in claim 1, wherein the image processing unit is configured to identify the boundary line by determining a plurality of reference points in each of the plurality of image.

5. The eye imaging apparatus in claim 4, wherein the plurality of reference points comprise at least one of the blood vessels, the intersections of blood vessels, the nerves, the intersections of the nerves of a posterior segment of the eye.

6. The eye imaging apparatus in claim 1, wherein the image processing unit is configured to establish a coordinate system with a plurality of reference points to determine positions of each of the plurality of images.

7. The eye imaging apparatus in claim 1, wherein the image processing unit is configured to process the plurality of images into a single composite image by blending pixels from clear portions of two overlapped images of the plurality of images.

8. The eye imaging apparatus in claim 1, wherein the image processing unit is configured to align the plurality of images by using a reference image, wherein the reference image is received with the same field of view through the optical imaging system.

9. A computer implemented syntactic image analyzing method to process a plurality of images of an eye with a same field of view under sequential illumination into a composite image, the method comprising:
    identifying a plurality of reference points in each of the plurality of images, wherein the plurality of reference points comprise at least one of the blood vessels, the intersections of blood vessels, the nerves, the intersections of the nerves of a posterior segment of the eye;
    analyzing each of the plurality of images to identify a boundary line of a clear portion in each of the plurality of images;
    adjusting the boundary line by gradually decreasing brightness of pixels near the boundary line away from the clear portion in each of the plurality of images;
    aligning the plurality of images by using the plurality of reference points, and
    combining the clear portion of each of the plurality of images into a single composite image.

10. The syntactic image analyzing method in claim 9, wherein analyzing each of the plurality of images comprises identifying the boundary line by determining a first sample area and a second sample area.

11. The syntactic image analyzing method in claim 9, wherein analyzing each of the plurality of images comprises identifying the boundary line by determining brightness of pixels in each of the plurality of images.

12. The syntactic image analyzing method in claim 9, wherein analyzing each of the plurality of images comprises identifying the boundary line by the plurality of reference points in each of the plurality of images.

13. The syntactic image analyzing method in claim 9, further comprising establishing a coordinate system with the plurality of reference points to determine positions of each of the plurality of images.

14. The syntactic image analyzing method in claim 9, further comprising processing the plurality of images into a single composite image by blending pixels from clear portions of two overlapped images of the plurality of images.

15. The syntactic image analyzing method in claim 9, further comprising aligning the plurality of images by using a reference image, wherein the reference image is received with the same field of view through the optical imaging system.

16. An eye imaging apparatus comprising:
    a housing,
    a light source disposed inside the housing comprising a plurality of light emitting elements each configured to illuminate a different portion of an eye time-sequentially, wherein one of the plurality of light emitting elements is configured to be activated at one time to illuminate one portion of the eye, the one portion having a greater average light intensity than other portions, and the one portion is located across an optical axis from the one of the plurality of light emitting elements;
    an optical imaging system having the optical axis and disposed inside the housing comprising an optical window, the optical window having a concave front surface configured to receive a portion of the eye;
    an image sensor disposed inside the housing configured to receive a plurality of images of the eye with a same field of view through the optical imaging system while each portion of the eye is illuminated time-sequentially by one of the light emitting elements; and
    a computing and communication unit disposed inside the housing comprising
        an image processing unit configured to analyze the plurality of images to identify a clear portion in each of the plurality of images by identifying a boundary line of the clear portion and to process the plurality of images into a single composite image, wherein the image processing unit is further configured to identify the boundary line by using an iterative sampling process and removing a false boundary that is a closed line resulted from pathologies in the eye;
        a display configured to display the plurality of images and the single composite image; and
        a wireless communication device configured to receive and transmit the plurality of images and the single composite image.

17. An eye imaging apparatus comprising:
    a housing,
    a light source disposed inside the housing comprising a plurality of light emitting elements each configured to illuminate a different portion of an eye time-sequentially, wherein one of the plurality of light emitting elements is configured to be activated at one time to illuminate one portion of the eye, the one portion having a greater average light intensity than other portions, and the one portion is located across an optical axis from the one of the plurality of light emitting elements;
    an optical imaging system having the optical axis and disposed inside the housing comprising an optical window, the optical window having a concave front surface configured to receive a portion of the eye;
    an image sensor disposed inside the housing configured to receive a plurality of images of the eye with a same field of view through the optical imaging system while each portion of the eye is illuminated time-sequentially by one of the light emitting elements; and
    a computing and communication unit disposed inside the housing comprising
        an image processing unit configured to analyze the plurality of images to identify a clear portion in each of the plurality of images by identifying a boundary line of the clear portion and to process the plurality of images into a single composite image, wherein the image processing unit is further configured to generate a homographic matrix for image registration and to apply the homographic matrix to adjust a plurality of reference points in each of the plurality of images to align the plurality of images;
        a display configured to display the plurality of images and the single composite image; and
        a wireless communication device configured to receive and transmit the plurality of images and the single composite image.

18. The syntactic image analyzing method in claim 9, wherein analyzing each of the plurality of images comprises identifying the boundary line by using an iterative sampling process and removing a false boundary that is a closed line resulted from pathologies in the eye.

19. The syntactic image analyzing method in claim 9, further comprising generating a homographic matrix for image registration, applying the homographic matrix to adjust the plurality of reference points in each of the plurality of images to align the plurality of images.

* * * * *